US009050214B2

(12) United States Patent
Gause et al.

(10) Patent No.: US 9,050,214 B2
(45) Date of Patent: *Jun. 9, 2015

(54) ABSORBENT DISPOSABLE INCONTINENCE PANTS COMPRISING SIDE SECTIONS

(75) Inventors: Enno Gause, Heidenheim (DE); Ruediger Kesselmeier, Herbrechtingen (DE); Krzysztof D. Malowaniec, Heidenheim (DE); Maximilian Swerev, Augsburg (DE)

(73) Assignee: Paul Hartmann AG, Heidenheim (DE)

( * ) Notice: Subject to any disclaimer, the term of this patent is extended or adjusted under 35 U.S.C. 154(b) by 385 days.

This patent is subject to a terminal disclaimer.

(21) Appl. No.: 13/257,983
(22) PCT Filed: Mar. 24, 2010
(86) PCT No.: PCT/EP2010/001819
§ 371 (c)(1),
(2), (4) Date: Sep. 21, 2011
(87) PCT Pub. No.: WO2010/108660
PCT Pub. Date: Sep. 30, 2010

(65) Prior Publication Data
US 2012/0035569 A1 Feb. 9, 2012

(30) Foreign Application Priority Data
Mar. 26, 2009 (DE) .......................... 10 2009 015 041

(51) Int. Cl.
*A61F 13/15* (2006.01)
*A61F 13/56* (2006.01)
(Continued)

(52) U.S. Cl.
CPC ....... *A61F 13/15756* (2013.01); *A61F 13/5616* (2013.01); *A61F 13/5638* (2013.01); *A61F 13/5655* (2013.01); *A61F 13/49014* (2013.01); *A61F 13/5622* (2013.01)

(58) Field of Classification Search
CPC . A61F 13/5622; A61F 13/56; A61F 13/5638; A61F 13/565; A61F 13/5655; A61F 13/58; A61F 2013/5666; A61F 2013/5677; A61F 2013/586; A61F 2013/587; A61F 2013/588
USPC ............. 604/385.24, 385.25, 385.26, 385.27, 604/385.29, 385.3, 385.22, 387, 396, 394
See application file for complete search history.

(56) References Cited

U.S. PATENT DOCUMENTS

| 6,004,306 A | 12/1999 | Robles |
| 8,114,059 B2 | 2/2012 | Ehrnsperger |

(Continued)

FOREIGN PATENT DOCUMENTS

| DE | 199 15 932 | 10/2000 |
| DE | 10 2006 050 971 | 4/2008 |

(Continued)

*Primary Examiner* — Jacqueline Stephens
(74) *Attorney, Agent, or Firm* — Paul Vincent

(57) ABSTRACT

The invention relates to a disposable absorbent incontinence diaper (2) of the open type, having a main part (4), comprising a front region (6) having front lateral longitudinal edges (42), a rear region (8) having rear lateral longitudinal edges (41) and a crotch region (10) that is located in between in the longitudinal direction (28) and comes to lie between the legs of a user, wherein the main part (4) comprises an absorbent pad (12), and having rear side portions (20) that are attached to the rear region (8) on both sides and front side portions (22) that are attached to the front region (6) on both sides, said rear and front side portions extending in the transverse direction (30) beyond the lateral front and rear longitudinal edges (42, 41) of the main part (4), and wherein the rear side portions (20) have first closure means (32) which are close to the leg opening and have closure aids and wherein the closure means (32) can be secured in a detachable manner at least on the outer side of the front side portions (22), as a result of which the front region (6) and the rear region (8) can be connected together, wherein, in order to form side-portion leg-opening regions (51, 52), the side portions (20, 22) are formed, at least on the side facing the crotch region (10), in a manner extending obliquely with respect to the longitudinal direction (28) or in a curved manner, characterized in that the length-to-width ratio R of the side-portion leg-opening region of the rear side portions (20) is 0.1-0.4, in that the tear propagation resistance Fm of the material forming the side portions is at least 4.0 N in the longitudinal direction of the diaper, and in that the spacing C of the closure means (32) close to the leg opening from the lower edge of the rear side portions is at most 5 cm.

14 Claims, 8 Drawing Sheets

(51) Int. Cl.
*A61F 13/58* (2006.01)
*A61F 13/49* (2006.01)

(56) References Cited

U.S. PATENT DOCUMENTS

| | | |
|---|---|---|
| 8,202,390 B2 | 6/2012 | Malowaniec |
| 8,251,967 B2 * | 8/2012 | Malowaniec et al. .... 604/385.01 |
| 8,454,782 B2 | 6/2013 | Ostertag |
| 8,556,878 B2 | 10/2013 | Malowaniec |
| 2003/0226862 A1 | 12/2003 | Vogt |
| 2006/0282053 A1 | 12/2006 | Rohrl |
| 2007/0267149 A1 | 11/2007 | McCabe |
| 2008/0208152 A1 | 8/2008 | Eckstein |

FOREIGN PATENT DOCUMENTS

| | | |
|---|---|---|
| EP | 0 263 720 | 4/1988 |
| EP | 1 719 484 | 11/2006 |
| EP | 1 941 853 | 7/2008 |
| JP | 1-89905 | 6/1989 |
| JP | 4 261 655 | 9/1992 |
| JP | 2005500135 | 1/2005 |
| JP | 2008-148942 | 7/2008 |
| JP | 2008-272250 | 11/2008 |
| JP | 2009511139 | 3/2009 |
| WO | WO 02/17843 | 3/2002 |
| WO | WO 2004/017882 | 3/2004 |
| WO | WO 2005/102241 | 11/2005 |
| WO | WO 2009/002235 | 12/2008 |
| WO | WO 2009/015746 | 2/2009 |

* cited by examiner

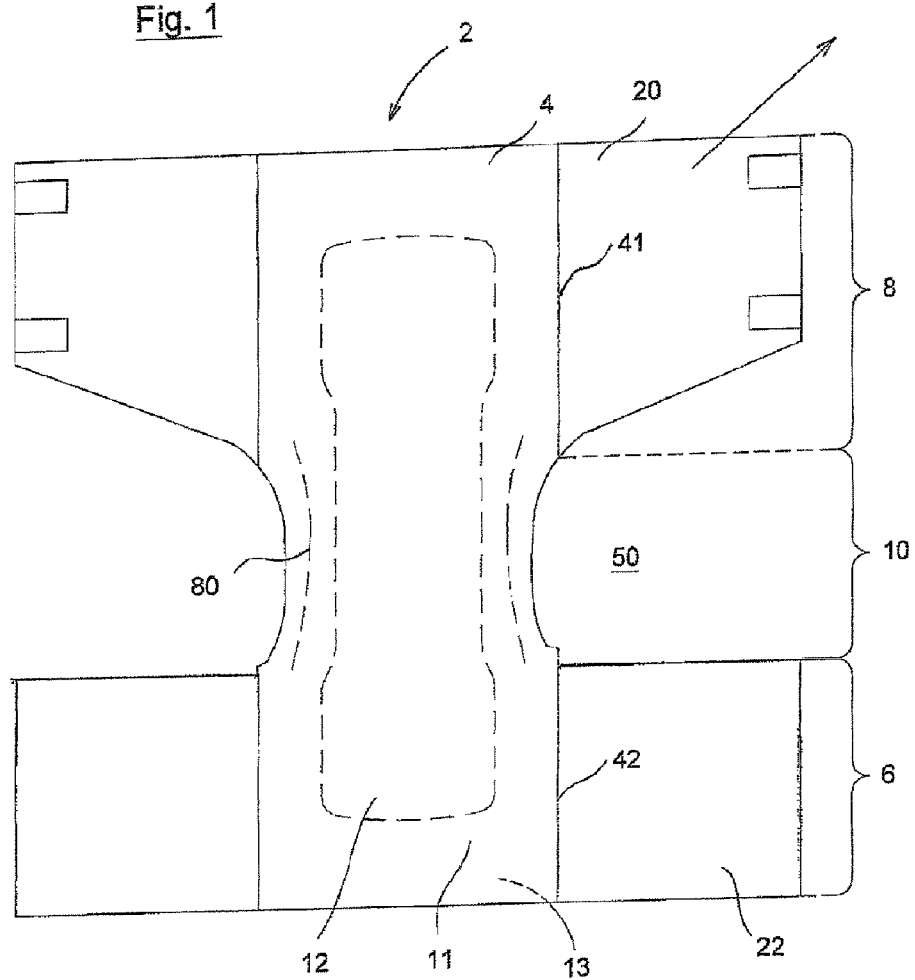

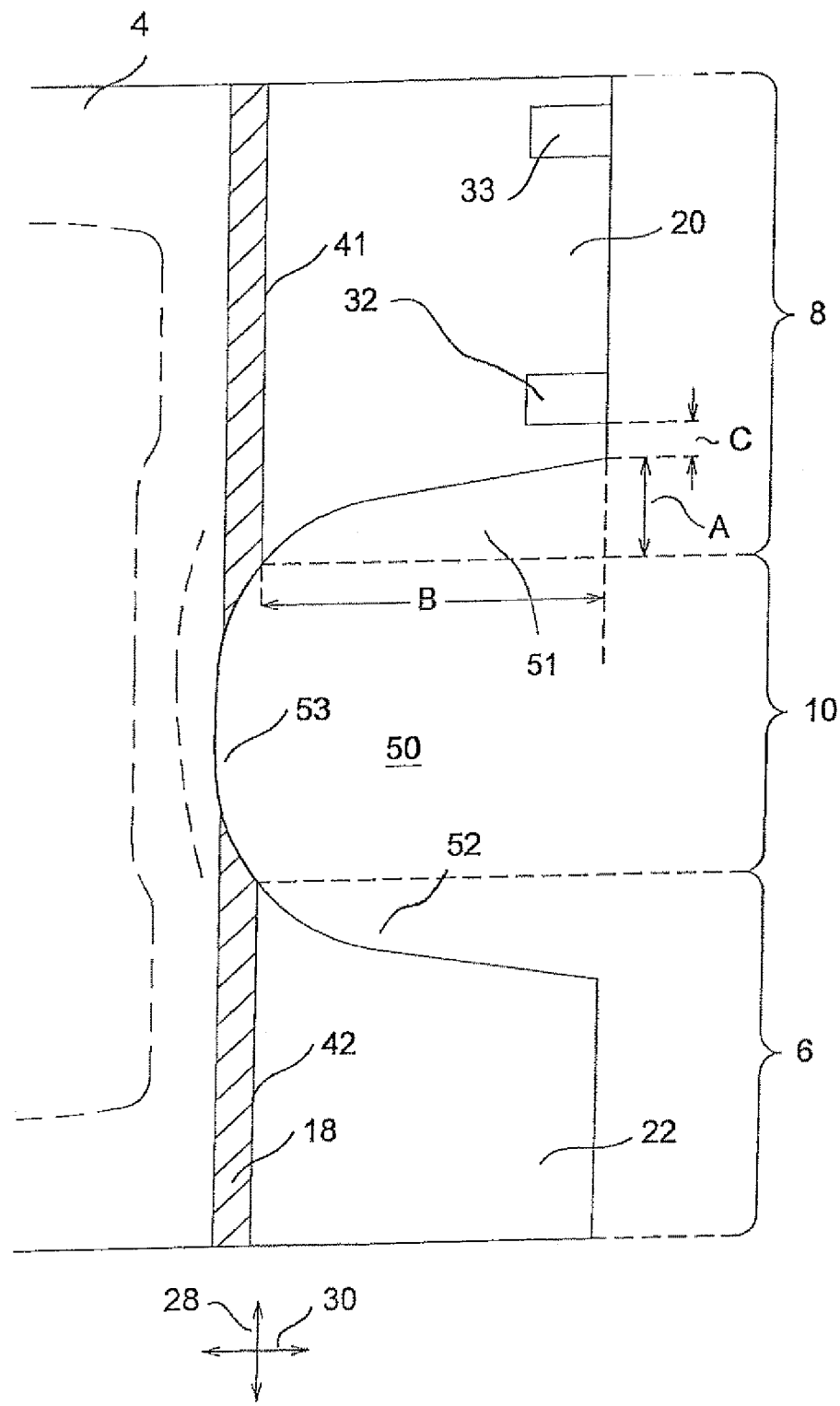

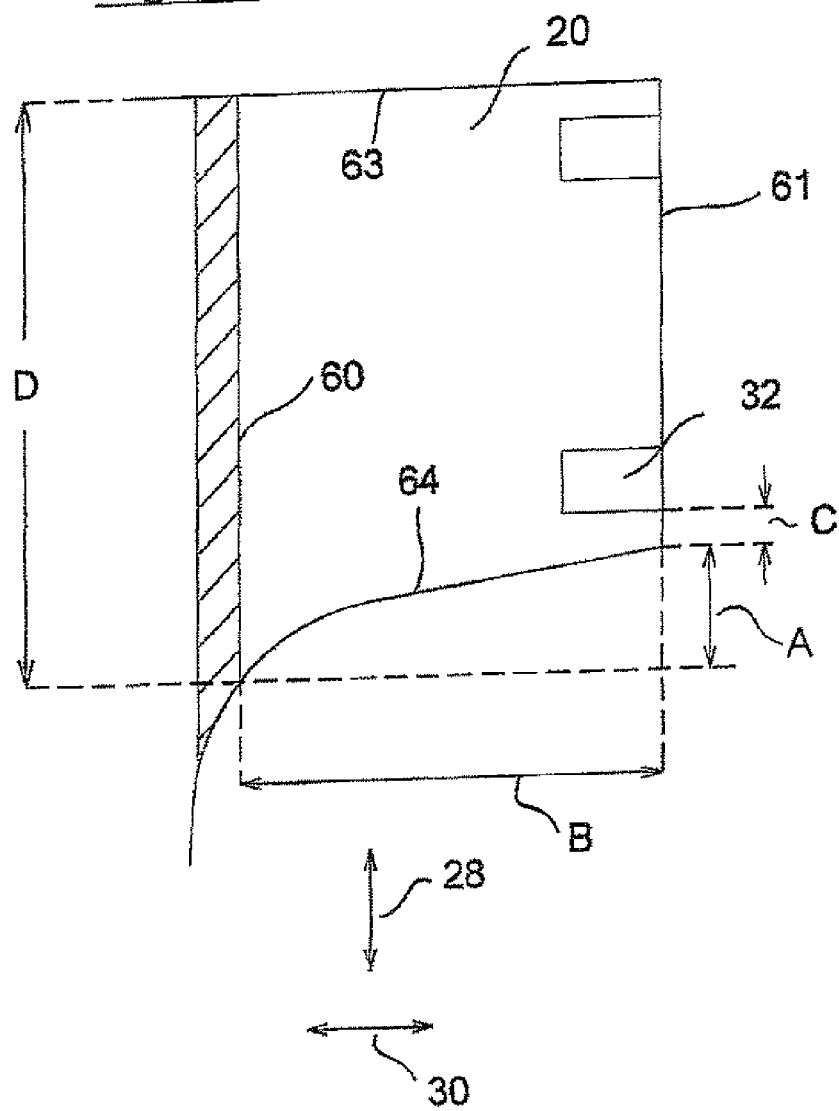

ABSORBENT DISPOSABLE INCONTINENCE PANTS COMPRISING SIDE SECTIONS

This application is the national stage of PCT/EP2010/001819 filed on Mar. 24, 2010 and claims Paris Convention Priority of DE 10 2009 015 041.2 filed Mar. 26, 2009.

BACKGROUND OF THE INVENTION

The invention relates to an absorbent incontinence article of the open type, having a main part, consisting of a front region, a rear region and a crotch region that is located in between in the longitudinal direction and comes to lie between the legs of a user, wherein the main part comprises an absorbent pad, and having separate side portions that are attached to the rear region and/or to the front region on both sides, are provided with closure means, extend in the transverse direction beyond lateral longitudinal edges of the main part and connect the front region and the rear region together in the put-on state of the article.

Incontinence articles of this kind are known and described, for example, in WO 2005/102241 A1. The side portions, which are sometimes also referred to as ears, are preferably attached directly to the main part, the chassis of the sanitary article, in a cut and place method. This manufacturing technology makes it possible to manufacture the side portions from a different raw material than the central main part of the sanitary article. For example, the side portions can be configured in an air-permeable manner, whereas the central main part can be formed in a substantially moisture-impermeable manner.

The most efficient and simplest, and also most cost-effective, shape of the side portions from a manufacturing point of view is the rectangular shape. This allows the materials forming the side portions to be transported during production in the form of an endless web of flat material from which the side portions are then severed transversely to the machine direction. There are virtually no offcuts in this case.

However, it has been shown that, particularly during the formation of the side portions in the otherwise advantageous rectangular form, when the sanitary article is being put on and while it is being worn, the problem sometimes occurs that the attached side portions can tear in the region of the lateral longitudinal edges of the main part. It has specifically been shown that, when users put on the sanitary article, they tend to exert a pull on the side portions obliquely to the transverse and longitudinal directions of the sanitary article, this being indicated in FIG. 1 by way of an obliquely upwardly inclined arrow. In such cases, it is possible for side portions to tear along the lateral longitudinal edges of the main part, with the tear propagating from the transverse edge, facing the crotch region, of the side portion. Hitherto, attempts have been made to improve the attachment of such side portions to the main part of sanitary articles by an optimum joining pattern, as per WO 2004/017882 A2 and WO 02/17843 A2.

A further proposal known from the prior art is to provide the side portions with a reinforcement means which, as seen in the transverse direction, is formed in a narrower manner than each side portion and which is provided at least in a region bridging the longitudinal side edge of the main part, that is to say overlays both a lateral longitudinal edge region of the main part and also a part of the side portion in the transverse direction (DE102006050971A1).

The present invention is based on the object of solving the problem outlined above in a more effective manner, that is to say to create absorbent incontinence articles having at the front and the rear in each case two laterally joined and attached side portions, in the case of which the tearing behavior of the side portions is significantly improved.

SUMMARY OF THE INVENTION

In the case of an absorbent incontinence article of the type mentioned at the beginning, this object is achieved according to the invention in that, in order to form a side-portion leg-opening region, the rear side portions are formed, at least on the side facing the crotch region, in a manner extending obliquely with respect to the longitudinal direction or in a curved manner, furthermore, in that each side-portion leg-opening region of the rear side portions has a length-to-width ratio $R=A/B$ of 0.1-0.4, furthermore, in that the tear propagation resistance $F_m$ of the material forming the rear side portions is at least 4.0 N in the longitudinal direction of the diaper, and in that the spacing C of the closure means close to the leg opening from the lower edge, facing the crotch, of the rear side portions is at most 5.0 cm. In this case, R, $F_m$ and C are determined as described further below.

As will be shown and explained in more detail below, even the contouring of the side portions results in a significant increase in the side-portion tear strength, since in the case of the contoured shape, the side edge of the main part is less suitable for forming a kind of tear-off edge for the side portions. In addition, the tensile force that is introduced into the side portion via the closure means close to the leg opening when the diaper is put on is distributed over a relatively large surface area, and so the resultant force that acts on the critical point is considerably reduced. The critical point is understood to be the point at which the lower edge of the side portion meets the rear side edge of the main part.

Even a very low length-to-width ratio $R=A/B$ of the side-portion leg-opening regions is sufficient to exert a significantly positive effect in this regard. A value R of greater than 0.4 would, however, be detrimental to the fit and to the comfort of putting on the disposable incontinence diaper and would moreover increase the quantity of offcut to be disposed of.

It was also found that the tear propagation resistance of the material forming the side portions of only at least 4.0 N combined with the contouring according to the invention of the side portions allows the closure means to be positioned very close to, that is to say at most 5 cm from, the lower edge of the rear side portions. Although it was found that the above-described risk of the side portions tearing along the lateral longitudinal edges of the main part decreases with spacing of the closure means from the lower edge of the side portions, at the same time, this was associated with a considerable loss of comfort in putting the diaper having the side portions that extend very far in the longitudinal and transverse directions of the diaper onto a person with a precise fit. Putting on the diaper with a precise fit is very much easier to carry out with closure means that are positioned very close to the lower edge of the side portions, since as a result a pull can be exerted over virtually the entire length of the side portions via the closure means. Surprisingly, the invention solves this hitherto unknown conflict of objectives by the combination of features specified in the independent claim. The present invention moreover allows a high degree of flexibility in the choice of materials for the rear side portions, since as a result materials having a high wearing comfort but low tensile strength can also be used.

Although generic incontinence diapers having side portions that are formed in a manner extending obliquely to the longitudinal direction or in a curved manner are already known (WO2009/015746A1), WO2009/015746A1 discloses neither the problem underlying the present invention nor the solution thereto.

Advantageously, the side-portion leg-opening regions formed in a manner extending obliquely to the longitudinal direction or in a curved manner are formed by a continuously or quasi-continuously guided severing process, particularly by cutting or punching, and so a continuous edge is formed. The path of the severing process in this case takes in the rear side portion, the main part and the front side portion. The leg-opening regions are thus formed exclusively by cutting or separating edges of the single, continuous or quasi-continuous severing process, thereby of course also implying that the disposable incontinence diaper can be produced in an economic manner and undesired edges are avoided.

In this severing process, the coherent offcut formed by the rear side portion, main part and front side portion has to be removed from the process in any case. This is carried out in an advantageous manner by the method described in DE102008056220. In this regard, full and express reference is made to the disclosure content of DE102008056220.

Preferably, the greatest longitudinal extent $l_1$, $l_2$ of the region severed from the rear and/or front side portion is 20-180 mm, particularly 30-100 mm. The extent $l_3$, in the longitudinal direction of the disposable incontinence diaper, of the region of the offcut severed from the main part is preferably from 110 to 500 mm, particularly from 200 to 450 mm; by contrast, the greatest transverse extent $l_4$ of this region severed from the main part is rather small and is preferably from 5 to 100, particularly from 8 to 70 and more particularly from 10 to 60 mm.

The extent $l_5$ of the offcut in said transverse direction is particularly from 150 to 350 mm, and more particularly from 190 to 300 mm.

In a further refinement of the invention, it is proposed for the length-to-width ratio R=A/B of the rear side-portion leg-opening regions to be at least 0.15, preferably 0.18-0.35, particularly preferably 0.20-0.32.

According to a further concept of the invention, the spacing C of the closure means from the lower edge, facing the crotch, of the rear side portions is at most 4.0 cm, preferably at most 3.5 cm, particularly preferably at most 3 cm and very particularly at least 0.5 cm.

The basis weight of the material forming the rear side portions should preferably be 14-40 g/m$^2$, particularly 16-30 g/m$^2$, and very particularly 17-28 g/m$^2$.

The tear propagation resistance of the material forming the rear side portions, measured and determined as average force Fm, as described in more detail below, is preferably at least 5.0 N, particularly preferably at least 6.0 N and very particularly preferably at least 6.5 N, but preferably at most 10.0 N.

The tear propagation resistance of the material forming the rear side portions, measured and determined as average of the force peaks Fm.sp, as described in more detail below, is preferably at least 5.5 N, particularly preferably at least 6.0 N, very particularly preferably at least 6.5 N and particularly at least 7.0 N, but preferably at most 12 N.

The tear propagation resistance of the material forming the rear side portions, measured and determined as maximum peak force Fsp, as described in more detail below, is preferably at least 5.5 N, particularly preferably at least 6.0 N, very particularly preferably at least 6.5 N and particularly at least 7.0 N, but preferably at most 12 N.

In a further development of the invention, it has been found to be advantageous also to provide the front side portions with a length-to-width ratio R and/or with a basis weight as described above for the rear side portions. Preferably, the front side portions furthermore also have a tear propagation resistance Fm and/or Fm.sp and/or Fsp as described for the rear side portions.

According to a preferred embodiment of the invention, an inner edge and outer edge of the front and/or rear side portions run parallel to one another. More preferably, the inner and/or outer edges run at least in portions parallel to a longitudinal direction of the disposable incontinence diaper. Preferably, the inner edge has a greater extent D in the longitudinal direction than the outer edge.

It has further been found to be advantageous to form the front and/or rear side portions from a nonwoven material. In particular all nonwoven materials which contain at least one formulation component based on a thermoplastic polymer are suitable. The nonwovens may contain fibers of PE, PP, PET, rayon, cellulose, PA and mixtures of these fibers. Bicomponent and multicomponent fibers are also conceivable and advantageous. In particular, carded nonwovens, spunbonded nonwovens, water-jet needled nonwovens, SM nonwovens, SMS nonwovens, SMMS nonwovens or else laminates of one or more of these kinds of nonwoven, wherein S stands for spunbonded nonwoven layers and M for meltblown nonwoven layers, are advantageous. It is furthermore conceivable and advantageous to form the front and/or rear side portions from a nonwoven-film laminate. In such a case, the film component would come to lie on the outside and the nonwoven component on the inside in order to ensure that a soft surface faces the body. As a development of this concept of the invention, it is advantageous to form the front and/or rear side portions from a nonwoven-film-nonwoven laminate, in which a film component is arranged in the manner of a sandwich between two nonwoven components.

Furthermore, it has been found to be advantageous that, laterally next to the longitudinal edges of the absorbent pad, first elastic elements having a component in the longitudinal direction are attached to the main part. These elastic elements can extend exactly in the longitudinal direction, that is to say in a straight line, or, particularly advantageously, also be provided such that they follow a certain contouring along the leg openings. In such a case, the elastic elements take a curved path along the leg opening. In a particular development of this concept of the invention, it is provided that the elastic elements do not extend into the side portions, but are limited to a positioning within the main part. Furthermore, second elastic elements made to extend in the first longitudinal direction, in particular in the form of what are known as upright cuff elements, which are known per se, for example including from EP0263720A1, may be attached to the web of the main part of the diaper. These preferably upright second elastic elements flank to a certain extent a center of the main part of the diaper or absorbent pad; they may be provided in the region of the edges of the absorbent pad, within the edges of the absorbent pad or outside the edges of the absorbent pad. They form a lateral run-out guard for the disposable incontinence diaper.

In a development of the invention, it is provided that, in order to secure the disposable incontinence diaper as intended on the body of a person, the closure means can be secured in a detachable manner at least in regions both to the outer side of the main part and also to the outer side of the front side portions, with the retaining forces between the closure means and the outer side of the front side portions preferably being greater than the retaining forces between the closure means and the outer side of the main part. This makes the user in most cases secure the closure means to the front side portions. The retaining forces determined as over-the-stomach retaining forces between the closure means, which have in particular mechanical closure aids, and the outer side of the main part are preferably 20-57 N/25 mm, particularly 25-50 N/25 mm. Furthermore, the over-the-stomach retaining forces between the closure means and the outer side of the side parts in the front region are preferably 58-90 N/25 mm, particularly 60-80 N/25 mm. Furthermore, it has been found to be advantageous for the over-the-stomach retaining forces between the closure means and the outer side of the rear side portions to be lower than the over-the-stomach retaining forces between the closure means and the outer side of the front side portions. This, too, makes the user in most cases secure the closure means to the front side portions. In the context of the present invention, the over-the-stomach retaining forces were determined by the test method described in WO2008049546A1.

The outer side of the main part of the disposable incontinence diaper is preferably formed by a nonwoven material, at least in regions, but particularly over the entire surface area. This gives the disposable incontinence diaper a "textile-like" impression. In such a case, it is advantageous to form the back sheet of the main part from a nonwoven-film laminate, with the nonwoven layer coming to lie on the outside and the film layer on the inside directed toward the absorbent pad, so that the nonwoven layer forms the outer side of the main part. This both ensures the liquid-impermeability of the main part and ensures the skin-friendly nature of the diaper. The film layer of this nonwoven-film laminate is then preferably formed from a one- or multi-layer liquid-impermeable, but preferably nevertheless breathable, film, with the breathability of the front and/or the rear side portions preferably being greater than the breathability of the nonwoven-film laminate forming the back sheet of the disposable incontinence diaper.

Advantageously, the rear side portions differ from the front side portions with regard to at least one, particularly at least two, more particularly at least three, and more particularly at least four, of their primary properties selected from the group comprising type of material, basis weight, breathability, density, stretchability, closure force, surface extent, thickness, and color. In this regard, express reference is made to the disclosure content of WO2009/015746.

In a development of the invention, it has been found to be advantageous for the length of the front and/or rear side portions, that is to say their maximum extent in the longitudinal direction of the diaper, to be at least 10 cm, particularly at least 15 cm, more particularly at least 18 cm, more particularly at least 22 cm and more particularly at most 45 cm. Advantageously, the overall length of the disposable incontinence diaper is 50-120 cm, particularly 60-110 cm and more particularly 70-110 cm. In a development of the invention, it has been found to be advantageous for the width of the front and/or rear side portions, that is to say the maximum extent of the side portions beyond the side edge of the main part of the diaper, to be 10-40 cm, particularly 12-30 cm, more particularly 13-25 cm. Preferably, the front side portions are the same width as the rear side portions.

The invention also relates to a method for producing a disposable incontinence diaper, wherein, in order to contour the leg-opening regions on both sides of the disposable incontinence diaper, a respective continuously or quasi-continuously guided severing process taking in the rear side portion, which is already provided with closure means, the main part and the front side portion is executed on each side, so that a coherent offcut which has to be removed is formed from the rear side portion, main part and front side portion, and as a result of which the spacing C of the closure means from the lower edge of the rear side portions is produced.

In a development of this method, it is provided that the offcut is gripped and removed by a transfer roller having pin-like, nub-like, hook-like or barb-like mechanical elements that protrude from its surface.

Preferably, in order to grip the offcut use is furthermore made of a negative-pressure assistance means at the transfer roller.

The method according to the invention is furthermore advantageously developed in that the extent $l_5$ of the offcut (cf. FIG. 6) in the transverse direction is 150 mm-350 mm, particularly 190 mm-300 mm. Preferably, the extent $l_3$ in the longitudinal direction of the region of the offcut severed from the main part is from 110 to 500 mm, particularly from 200 to 450 mm. More preferably, the transverse extent $l_4$ of the region of the offcut severed from the main part is from 5 to 100 mm, particularly from 8 to 70 mm, more particularly from 10 to 60 mm. More preferably, the greatest longitudinal extent $l_2$, $l_2$ of the region severed from the rear and/or front side portion is from 20 to 180 mm, particularly from 30 to 100 mm.

BRIEF DESCRIPTION OF THE DRAWING

In the drawing:

FIG. 1 shows a schematic illustration of a plan view of an incontinence article having side portions attached on both sides;

FIGS. 2a and 2b each show an enlarged partial view of the disposable incontinence diaper according to FIG. 1;

DESCRIPTION OF THE PREFERRED EMBODIMENT

Figure 3:
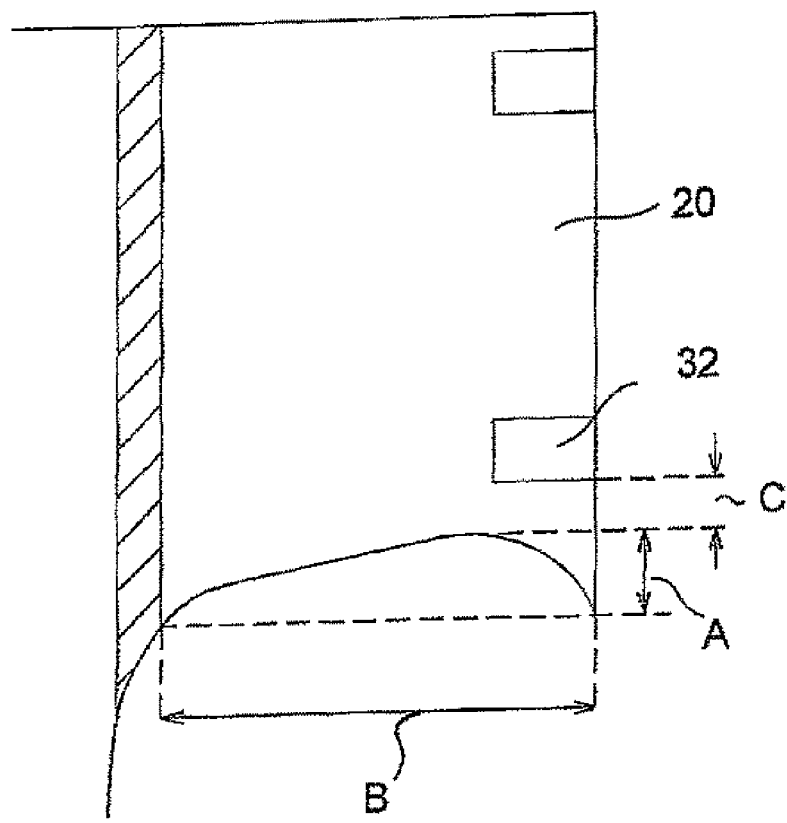
FIG. 3 shows by way of example a further side-portion geometry according to the invention.

FIG. 1 schematically shows a plan view, not to scale, of the inner side, that is to say the side facing the body, of a disposable absorbent incontinence diaper 2 in the just-unfolded state. The disposable incontinence diaper 2 comprises a main part 4 having a front region 6, a rear region 8 and a crotch region 10 located in between in the longitudinal direction. Also indicated is an absorbent pad 12, which is usually arranged between chassis-forming materials of the main part 4, that is to say particularly between a liquid-permeable top sheet 11, which is formed from a nonwoven material, and a substantially liquid-impermeable back sheet 13, which is formed from a film material, of the main part 4. The back sheet 13 can also be formed from a liquid-impermeable nonwoven material or from a nonwoven-film laminate, with the nonwoven layer then coming to lie on the outside and the film layer on the inside directed toward the absorbent pad. This gives the disposable incontinence diaper 2 a "textile-like" impression. Laterally next to the longitudinal edges of the absorbent pad 12, first elastic elements 80 are attached to the main part 4, between the top sheet 11 and the back sheet 13. The elastic elements 80 extend substantially in the longitudinal direction, that is to say with a substantial component in the longitudinal direction, in which case they take a curved path along the leg-opening region portion to be assigned to the crotch region 10. The disposable incontinence diaper 2 furthermore comprises front side portions 22 and rear side portions 20, which are attached to the main part 4 as separate nonwoven components on both sides. As is shown in an enlarged illustration, not to scale, of a partial view of FIG. 1 (FIG. 2a), the side portions 20, 22 are connected in a nondetachable manner in an overlapping region 18, which is illustrated in a hatched manner, to chassis-forming materials of the main part 4, that is to say, for example, to the back sheet 13 and/or the top sheet 11. The side portions 20, extend beyond the front and rear lateral longitudinal edges 42, 41 of the main part in the transverse direction 30.

The front and rear lateral longitudinal edges 42, 41 of the main part are understood in the context of the present invention to mean those longitudinal edge regions of the main part to which the side portions are attached and beyond which said side portions extend.

The longitudinal extent of the front and rear side edges 42, 41 of the main part thus also define the longitudinal extent of the front region 6 and of the rear region 8 of the disposable incontinence diaper 2.

Hereby, it is also made clear that the expressions "side edge" and "lateral longitudinal edge" are used as synonyms in the preceding and following text.

The side portions 20, 22 are conceived of and intended for being connected to one another in the put-on state of the disposable incontinence diaper 2, in order to form a hip region of the sanitary article that is continuous in the circumferential direction. In this case, the side portions 20, 22 provided on one side of the main part 4 are in each case connected together. To this end, mechanical closure means 32 close to the leg opening and closure means 33 remote from the leg opening, particularly having mechanical closure aids such as burr hooks, are provided on the rear side portions 20 and can be secured in a detachable manner to the outer side of the front and rear side portions 20, 22. Preferably, the closure means can also be secured in a detachable manner to the outer side of the main part. Both the front side portions 22 and the rear side portions 20 are formed from a nonwoven material, in the illustrated case from a PP spunbonded nonwoven, Pegatex S, manufacturer: Pegas a.s., Primetická 86, 66904 Znojmo, CZ. The basis weight of the nonwoven material of the front side portions is 30 g/m². The fiber thickness of the fibers forming the nonwoven material is 2 dtex. The over-the-stomach retaining forces between the closure means 32 and the outer side of the front side portions 22 are preferably at least 58 N/25 mm.

The basis weight of the nonwoven material of the rear side portions 20 in the illustrated case is 27 g/m².

The tear propagation resistance of the nonwoven material of the rear side portions, measured in the longitudinal direction 28, is:
Fm: 7.0 N
Fm.sp: 7.2 N
Fsp: 9.8 N.

The over-the-stomach retaining forces between the closure means 32, 33 and the outer side of the rear side portions 20 are lower than the over-the-stomach retaining forces between the closure means 32, 33 and the outer side of the front side portions 22.

As can be seen from FIG. 1, the rear side portions 20 have a larger surface extent than the front side portions 22.

The front and rear side portions thus differ in at least three of their primary properties, namely the basis weight, the closure force and the surface extent.

The difference in closure force between the front and rear side portions makes the user secure the closure means 32, 33 preferably to the front side portions 22, this being beneficial to the fit of the diaper. As can further be gathered from FIG. 1, the leg-opening regions 50 are formed by front and rear side portions 20, 22, which are formed in a curved manner toward the crotch region and form the side-portion leg-opening regions, and by the hourglass-shaped contouring of the main part 4. An hourglass-shaped contouring of the main part is understood here to mean any shape of the narrowing in the main part 4 in the crotch region 10, that is to say any curved, and also any non-curved or not exclusively curved shape, in which case the crotch region 10 of the main part 4 has a shorter extent in the transverse direction 30 than the front region 6 and/or the rear region 8 of the main part.

The continuity of the leg opening 50 is formed by in each case a single cut, that is to say one on each side, said cut taking in both the side portions 20, 22 and the main part 4 and in the process being guided continuously through side-edge and main-part material to be separated. The leg opening 50 thus comprises a front side-portion leg-opening region 52, a rear side-portion leg-opening region 51 and the main-part leg-opening region 53 (FIG. 2a).

FIG. 2a also illustrates the positioning of the closure means 32 close to the leg opening at the spacing C and also the length-to-width ratio R=A/B. In order not to overburden FIG. 2a, FIG. 2b illustrates once more the rear side portion 20 having the spacings A, B and C that are necessary for determining the parameters according to the invention: the rear side portion 20 is bounded by an inner edge 60, which corresponds to the rear side edge 41 of the main part, by an outer edge 61, and by an upper edge 63 and a lower edge 64, which forms the contour of the side-portion leg-opening region. The upper edge 63 and the lower edge 64 connect the inner edge 60 to the outer edge 61. The inner edge 60 and the outer edge 61 preferably extend parallel to one another, more preferably, the inner edge 60 and/or outer edge 61 extend at least in portions parallel to a longitudinal direction 28 of the disposable incontinence diaper. The inner edge 60 preferably has a greater extent D in the longitudinal direction 28 than the outer edge 61.

In the context of the present invention, spacing A is defined as the greatest extent of the lower edge 64 in the longitudinal direction 28. Spacing B is defined as the greatest extent of the rear side portion in the transverse direction 30, that is to say the greatest distance between the inner edge 60 and the outer edge 61 in the transverse direction, and therefore the width of the side portion. Spacing C is defined as the shortest distance, to be determined in the longitudinal direction 28, between a closure means 32 close to the leg opening and the lower edge 64.

FIG. 3 shows an alternative side-portion geometry according to the invention, in which the greatest extent A of the lower edge 64 is to be measured in the longitudinal direction 28 between the outer edge 61 and the inner edge 60, since the contour of the lower edge 64 is at a true maximum.

In the case illustrated in FIGS. 2a and 2b, A is 55 mm, B is 225 mm, and R is thus 0.24. The length D of the inner edge 50 is 350 mm. The closure means 32 close to the leg opening is fastened by the manufacturer very close, at a spacing C=16 mm from the lower edge 54 of the rear side portion.

The tear strength of the rear side portions is 64.5 N. For comparison, the side-portion tear strength of a comparison diaper, which was manufactured from identical materials and had an identical maximum side-portion length and width, but was equipped with side portions having a rectangular contour (as is illustrated schematically in WO2005102241), was determined. Only the basis weight of the PP spunbonded nonwoven (manufacturer: Pegas a.s.) of the rear side portions was, at 30 g/m², slightly, i.e. around 3 g/m², heavier than that of the side portions of the above-described diaper according to the invention. The side-portion tear strength of this comparison diaper was only 38.8 N. This shows that even slight contouring, expressed by a low R value, has a clearly positive effect on the side-portion tear strength.

In the context of the present invention, the side-portion tear strengths are measured by means of the test method explained further below.

In the context of the present invention, the tear propagation resistances are determined as tear propagation strength by the test method specified in DIN EN ISO 13937-2. As a deviation from this, the sample length is 150 mm. The central incision has a depth of 50 mm. The speed of deformation is set to 200 mm/min. The evaluation takes place by means of an electronic device. As a deviation from DIN EN ISO 13937-2, a peak value to be evaluated is characterized by an increase or drop in force of at least 0.2 N. Thus, upper and lower force peaks are taken into account when the Fm.sp is being determined. Besides the arithmetic average value of the force peaks Fm.sp, the maximum value of all the upper force peaks of each specimen Fsp and the average force Fm calculated over the entire force characteristic curve to be evaluated are also determined.

Figure 4:
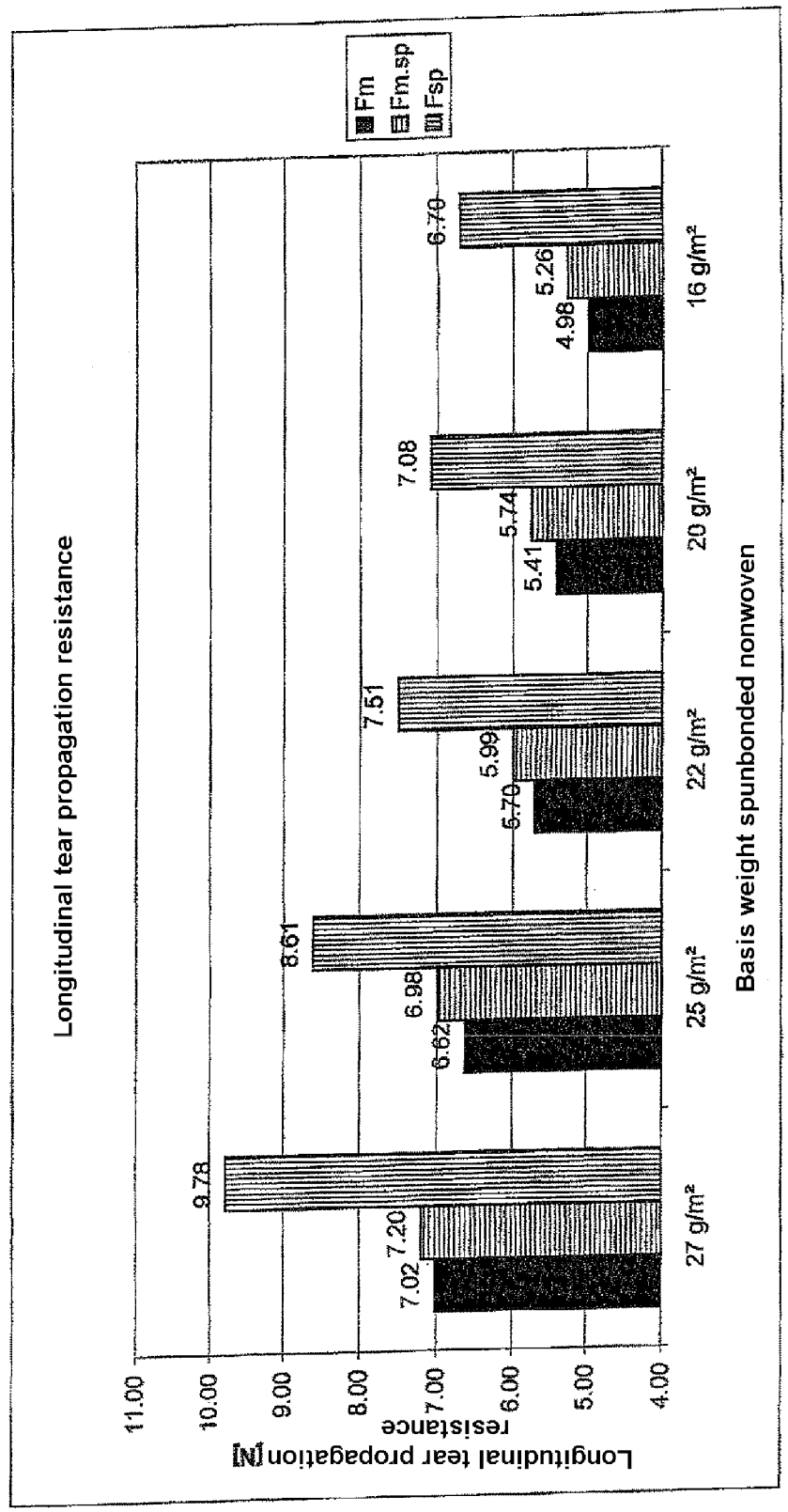
FIG. 4 shows a representation of determined tear propagation resistances in the form of a graph.

FIG. 4 shows a representation in the form of a graph of determined tear propagation resistances of spunbonded nonwoven materials forming side portions, said materials only differing from one another with regard to the basis weight. The side-portion tear strengths of disposable incontinence diapers according to the invention that are produced therefrom decrease as the tear propagation resistance of the side-portion materials drops. However, it was found with the present invention that the tested 16 g/m$^2$ spunbonded nonwoven having a tear propagation resistance of Fm 4.98 in combination with the contouring according to the invention of the side portions also meets the tear strength requirements of the side portions in use of the diaper, even though the closure means are fastened by the manufacturer less than 5 cm away from the lower edge of the side portions. Reference is expressly made to the fact that the provision of a basis weight of at least 16 g/m$^2$ is in no way a sufficient condition for ensuring the requisite tear propagation resistances. Rather, changing the basis weight of the nonwoven material is the simplest method for varying the tear propagation resistance with otherwise unchanged nonwoven characteristics. The kind of process for forming the nonwoven, the polymers used and the binding agent which may be used are only a few further options which are familiar per se to a person skilled in the art in order to affect the strengths of the nonwoven material.

Figures 5, 6:
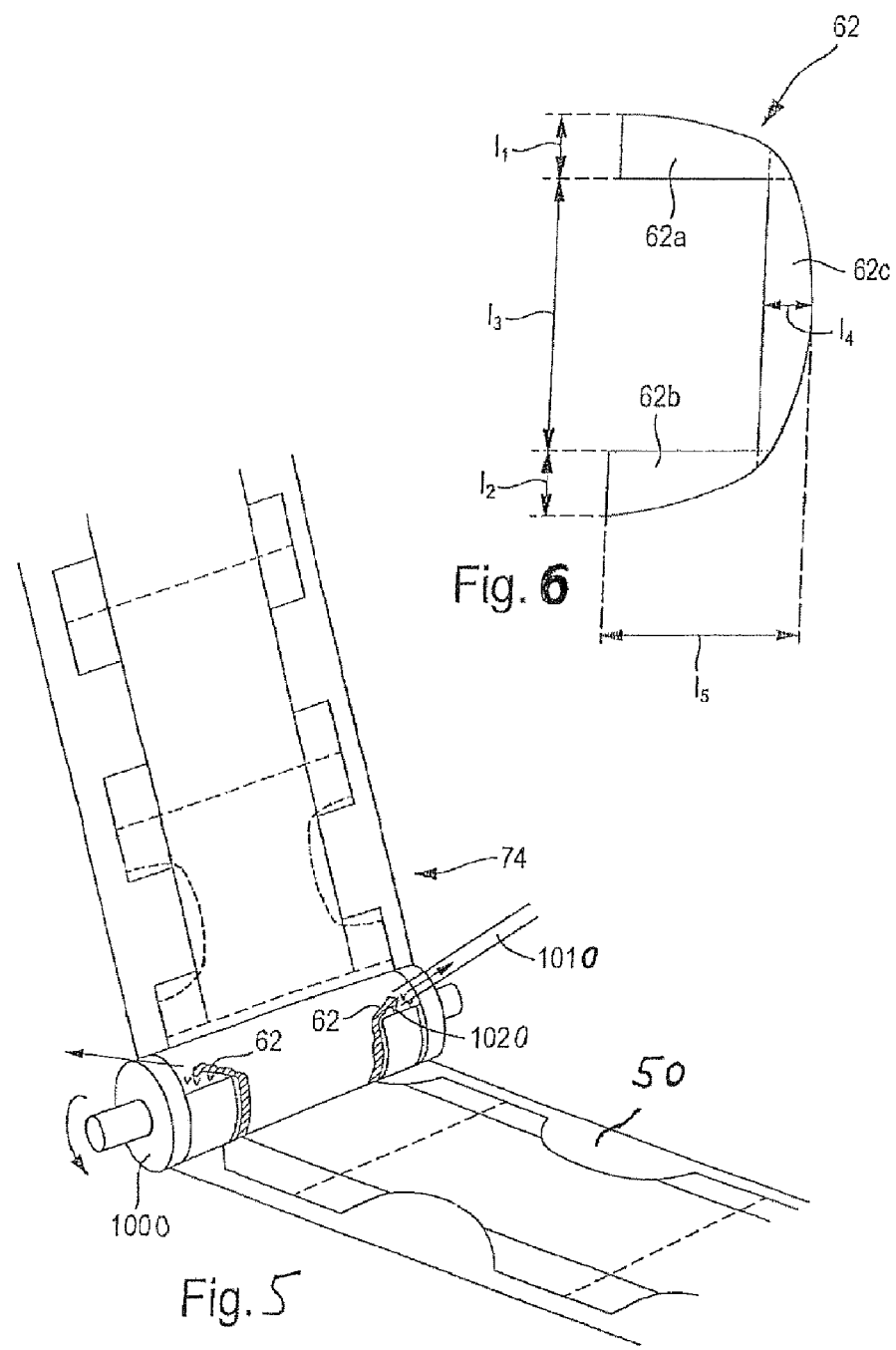
FIG. 5 shows a perspective view of the web guidance over a transfer roller having protruding mechanical elements for removing the offcut.
FIG. 6 shows an illustration of a severed offcut.

FIG. 5 schematically shows a detail from the method according to the invention for producing the disposable incontinence diaper. The web is guided over a transfer roller 1000 for removing the offcut 62, which roller is arranged downstream of the cutting rollers, not illustrated, at position 74 for contouring the leg-opening regions 50 on both sides and by means of which roller the coherent offcut 62 from the rear side portion, main part and front side portion can be removed from the process. To this end, the transfer roller 1000 has pin-like mechanical elements 1020, which are arranged in a zoned manner, for gripping the offcut 62. The offcut can be removed by suction, in particular after being gripped by the transfer roller 1000, by means of a suction device 1010 which is only indicated. With regard to the detailed design of the transfer roller, full reference is made to DE102008056220.

FIG. 6 shows schematically and not to scale the extent $l_5$ of the offcut 62 in the transverse direction of preferably 150 mm-350 mm, particularly 190 mm-300 mm. Preferably, the extent $l_3$ of the region 62c of the offcut severed from the main part is from 110 to 500 mm, particularly from 200 to 450 mm, in the longitudinal direction. More preferably, the transverse extent $l_4$ of the region 62c of the offcut severed from the main part is from 5 to 100 mm, particularly from 8 to 70 mm, more particularly from 10 to 60 mm. More preferably, the greatest longitudinal extent $l_1$, $l_2$ of the region 62a, 62b severed from the rear and/or front side portion is from 20 to 180 mm, particularly from 30 to 100 mm.

The present invention has thus been successful in providing for the first time a disposable incontinence diaper having front and rear side portions attached to the main part, said disposable incontinence diaper having sufficient side-portion tear strength in use of the diaper and also taking sufficient account of the comfort of putting on and wearing the disposable incontinence diaper.

Side-Portion Tear Strength Test Method

A disposable incontinence diaper is separated (cut or punched) 60 cm below the rear side portion, with the main part being damaged in the transverse direction. The specimen containing the lower side portion is clamped into the tensile testing instrument (see FIGS. 7 and 8).

Figure 7:
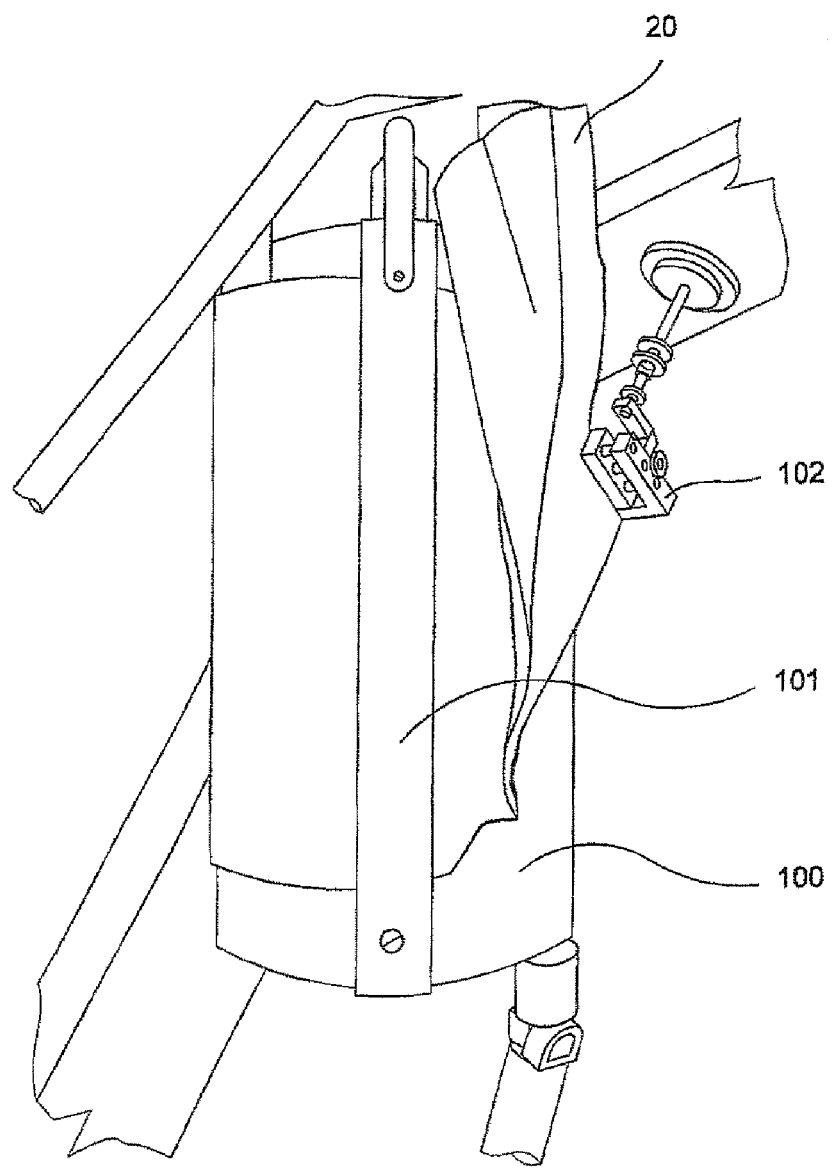
FIGS. 7 and 8 show an illustration of the testing of the side-portion tear strength.
Figure 8:
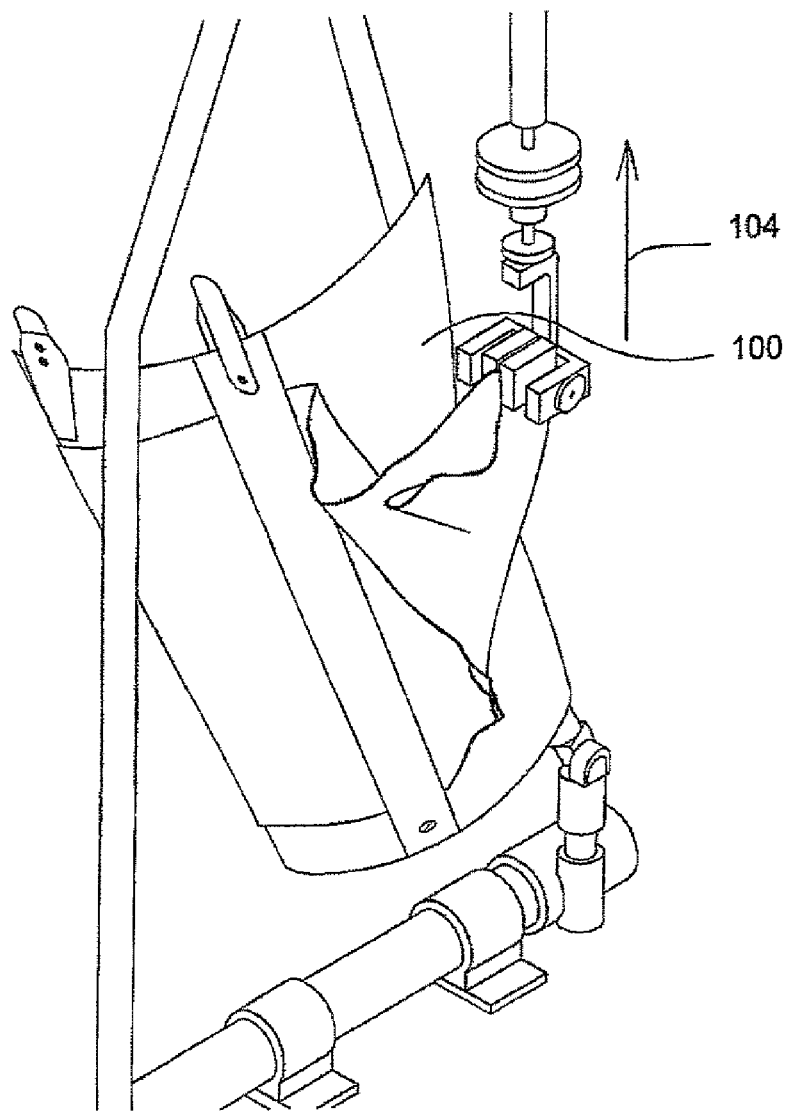

The specimen is in the process laid with its inner side resting against and over a curved surface 100 (radius of curvature 19 cm), intended to simulate the rounding of the back region of a user, and is clamped into the apparatus of the tensile testing instrument (see FIGS. 7 and 8). The testing of a right-hand rear side portion is illustrated. When a left-hand rear side portion is tested, provision is made of a mirror-inverted arrangement of test apparatus and arrangement.

The product is intended to be clamped into the apparatus such that the specimen is fixed by the stationary clamp 101 over the entire length of the specimen at a spacing (transverse direction) of 60 mm from the inner edge of the side portion 20. The movable clamp 102 is fixed at the lower end of the outer edge of the side portion 20 over a length of 60 mm and a width of 30 mm. The curved surface 100 is tilted forward (inclined) so that the side portion can rest against the curved surface during the subsequent tensile test (see FIG. 8). A tensile test is carried out by controlled movements of the movable clamp 102 in the direction of the arrow 104. The test speed at which the movable clamp 102 is moved mechanically away from the main part of the incontinence product is 1800 mm/min. In this case, an initial force of 0.2 N (Newton) is applied. The method ends as soon as the side portion tears over a length of at least 5 cm. Overall, a minimum number of n=5 tests should be carried out. For evaluation purposes, the maximum forces in [N] measured in each tensile test are averaged.

We claim:

1. A disposable absorbent incontinence diaper of an open type, the diaper comprising:
    a main part having an absorbent pad, a front region with front lateral longitudinal edges, a rear region having rear lateral longitudinal edges and a crotch region disposed in an intermediate location in a longitudinal direction and coming to lie between legs of a user;
    front side portions attached to said front region on both sides thereof; and
    rear side portions attached to said rear region on both sides thereof, said rear and front side portions extending in a transverse direction beyond said lateral front and rear longitudinal edges of said main part, said rear side portions having first closure means proximate to leg openings, said first closure means having closure aids, said closure means being structured for detachable connection to an outer side of said front side portions to join together said front region and said rear region, wherein, at least on sides thereof facing said crotch region, said front and said rear side portions extend obliquely or in a curved manner with respect to said longitudinal direction, thereby defining side-portion leg-opening regions, a length-to-width ratio R of said side-portion leg-opening regions of said rear side portions being 0.1-0.4 and material forming said rear side portions having a tear propagation resistance Fm of at least 4.0 N and of at most 10 N in said longitudinal direction of the diaper, wherein said closure means proximate said leg openings have a spacing C of at most 5 cm from an uppermost excursion of said side-portion leg-opening regions.

2. The disposable absorbent incontinence diaper of claim 1, wherein said length-to-width ratio R of said side-portion leg-opening region of said rear side portions is at least 0.15, 0.18 to 0.35 or 0.20 to 0.32.

3. The disposable absorbent incontinence diaper of claim 1, wherein said spacing C of said closure means is at most 4 cm, at most 3.5 cm, at most 3.0 cm or at least 0.5 cm.

4. The disposable absorbent incontinence diaper of claim 1, wherein said rear side portions have at least one further closure means which is remote from the leg openings and is provided with closure aids.

5. The disposable absorbent incontinence diaper of claim 1, wherein, in said longitudinal direction of the diaper, said tear propagation resistance Fm of material forming said rear side portions is at least 5.0 N, at least 6.0 N or at least 6.5 N.

6. The disposable absorbent incontinence diaper of claim 1, wherein, in said longitudinal direction of the diaper, a tear propagation resistance Fm.sp of material forming said rear side portions is at least 5.5 N, at least 6.0 N, at least 6.5 N, at least 7.0 N or at most 12 N.

7. The disposable absorbent incontinence diaper of claim 1, wherein, in said longitudinal direction of the diaper, a tear propagation resistance Fsp of material forming said rear side portions is at least 5.5 N, at least 6.0 N, at least 6.5 N at least 7.0 N or at most 12 N.

8. The disposable absorbent incontinence diaper of claim 1, wherein said front and rear side portions are formed from or comprise a nonwoven material.

9. The disposable absorbent incontinence diaper of claim 1, wherein an extent in said transverse direction of said front and side rear portions beyond said lateral edge of said main part of the diaper is 10-40 cm, 12-30 cm or 13-25 cm.

10. The disposable absorbent incontinence diaper of claim 1, wherein a length of said rear side portions has an extent in said longitudinal direction of the diaper of at least 10 cm, at least 15 cm, at least 18 cm, least 22 cm or at most 45 cm.

11. A method for producing the disposable incontinence diaper of claim 1, the method comprising the steps of:
   a) disposing the closure means on the rear side portions;
   b) performing continuously or quasi-continuously guided severing processes on both sides of the disposable incontinence diaper, thereby forming contour leg-opening regions, the severing process encompassing and generating a coherent offcut from the rear side portion, the main part and the front side portion, thereby defining the spacing C of the closure means close to the leg opening; and
   c) removing the coherent offcut.

12. The method of claim 11, wherein the offcut is gripped and removed by a transfer roller having pin-like, nub-like, hook-like or barb-like mechanical elements that protrude from a surface thereof.

13. The method of claim 12, wherein a negative-pressure assistance means disposed at the transfer roller grips the offcut.

14. The method of claim 11, wherein an extent of the offcut in the transverse direction is 150 mm to 350 mm or 190 mm to 300 mm and an extent in the longitudinal direction of a region of the offcut severed from the main part is 110 to 500 mm or 200 to 450 mm, wherein a transverse extent of the region of the offcut severed from the main part is 5 to 100 mm, 8 to 70 mm or 10 to 60 mm, and a greatest longitudinal extent of a region severed from the rear and/or front side portion is 20 to 180 mm or 30 to 100 mm.

* * * * *